United States Patent [19]

Azema et al.

[11] Patent Number: 5,147,352

[45] Date of Patent: Sep. 15, 1992

[54] OPTICAL SYSTEM FOR USE IN A SURGICAL APPARATUS

[75] Inventors: Alain Azema, 28, avenue des Arénes; Jean Botineau, 5, avenue Chateaubriand; Gérard Moulin, 167, avenue Maréchal Lyautey, all of Nice, France

[73] Assignees: Alain Azema; Jacques Arneodo, both of Nice; Jean Botineau, Valbonne; Philippe Crozafon, Nice; Gérard Moulin, Valbonne, all of France

[21] Appl. No.: 214,046

[22] Filed: Jun. 29, 1988

[30] Foreign Application Priority Data

Jul. 8, 1987 [FR] France .................................. 87 09703

[51] Int. Cl.$^5$ ............................................... A61N 5/06
[52] U.S. Cl. ........................................ 606/5; 606/17; 128/395; 359/739; 359/740
[58] Field of Search ........................... 128/303.1, 395; 350/448–450

[56] References Cited

U.S. PATENT DOCUMENTS

| 1,924,700 | 8/1933 | Thilo | 350/449 |
| 2,672,799 | 3/1954 | Terwilligen | 350/448 |
| 2,804,802 | 9/1957 | Loeck | 350/449 |
| 3,348,547 | 10/1967 | Kavanagh | 128/395 |
| 4,141,362 | 2/1979 | Wursta | 128/395 |

FOREIGN PATENT DOCUMENTS 13373 7/1883 United Kingdom ................ 350/449

Primary Examiner—David M. Shay
Attorney, Agent, or Firm—Fisher, Christen & Sabol

[57] ABSTRACT

This invention relates to an optical system, adapted to be disposed between a source capable of emitting a beam of light and a target. Near the upstream focal point of the first optics for focussing the beam, the beam provides an image which is at least substantially in section, but which, due to characteristics inherent in the beam of light, produces an image which is oblong in shape at the downstream focal point of the first optics for focusing the beam. The optical system successively comprises, in the direction of propagation of the beam, downstream of the first optics, first diaphragm disposed near the focal point of the first focussing optics, capable of removing a variable part of the area of the section of the beam at the focal point, and second focussing optics. The optical system may further include a second diaphragm disposed upstream from the first optics for focusing the beam for further limiting the ellipticity of the beam. The invention is more particularly applicable to a surgical apparatus for modifying the curvature of the cornea.

8 Claims, 2 Drawing Sheets

OPTICAL SYSTEM FOR USE IN A SURGICAL APPARATUS

BACKGROUND OF THE INVENTION

The present invention relates to an optical system adapted to be disposed between a source capable of emitting a beam of light and a target.

The invention is more particularly, but not exclusively, applicable to a surgical apparatus for modifying the curvature of the cornea.

Among the different known techniques for surgically treating certain disorders, such as myopia and hypermetropia, by modifying the curvature of the cornea, the elimination of corneal matter by photodecomposition by means of a beam of ultraviolet light produced by a laser source, in particular an excimer laser, is the most recent technique to have been envisaged.

An optical system, comprising in particular focussing optics, is disposed between the laser source and the eye, which system directs the beam onto the zone of cornea to be eliminated and forms a light spot on a part of said zone, said spot being capable of scanning the whole of said cornea zone.

However, due to characteristics inherent therein, the beam generated by the laser source is not always stigmatic, i.e. it sometimes presents, in the image focus of focussing optics, a section of oblong shape and not a circular "punctual" or quasi-punctual section. In this way, a light spot, maintaining a symmetry of revolution, i.e. which remains circular or virtually circular, cannot be obtained on the target, in the present case an eye, when said target is displaced relatively to said optics in the image space of the latter, which relative displacement is necessary to allow scanning by said light spot of the whole of the cornea zone to be eliminated.

SUMMARY OF THE INVENTION

It is an object of the present invention to overcome this drawback by providing an optical system adapted to maintain for a beam of light a quasi-symmetry of revolution in the image space of the system.

To that end, the optical system, adapted to be disposed between a source capable of emitting a beam of light and a target, of the type comprising first optics for focussing said beam of light, said beam presenting at the inlet of said optics an at least substantially circular section and, due to characteristics inherent in the beam of light, presenting at the image focus of said first focussing optics a section of oblong shape, is noteworthy, according to the invention, in that it successively comprises, in the direction of propagation of said beam, downstream of said first optics, first shaping means disposed in the image focus of said first focussing optics, and capable of removing a variable part of the area of the section of said beam in said image focus, and second focussing optics, with the result that, for any relative displacement of the target and said optical system in the image space of the system, said area removed by said means is adjustable so as to obtain, in said space at the level of the target, a section of beam which remains at least substantially circular.

In this way, when said optical system is used for example in a surgical apparatus for modifying the curvature of the cornea by photodecomposition by a beam of ultraviolet light, the light spot created on the eye may maintain, for the whole duration of the treatment, i.e. when the relative position of the eye and of the system varies in the image space of the system, a circular shape or, at the very least, a virtually circular shape of which the ellipticity is maintained within an acceptable limit.

As certain sources of ultraviolet light emit a beam of at least substantially rectangular section, the optical system in that case comprises, between said source and said first focussing optics, second means for diaphragming said beam, on leaving said source, along an at least substantially circular section.

In particular, said second means for diaphragming said beam may be disposed at least substantially near the focal point upstream from said first focussing optics.

Said second focussing optics are advantageously located, with respect to said first shaping means, at a distance equal to at least substantially twice the focal distance of said second optics.

According to another feature of the invention, said shaping first means are constituted by a diaphragm whose opening is in the form of a slot disposed transversely to the direction of propagation of the beam and of which the width varies between zero and the largest dimension of the oblong section of the beam at the location of said first shaping means, and said optical system comprises means for relative displacement between said diaphragm and the rest of said system transversely to the direction of propagation of the beam. These displacement means make it possible to diaphragm the beam to an adjustable width, less than or equal to the largest dimension of the oblong section of the beam.

The width of said beam advantageously varies continuously.

In particular, said displacement means are associated with said diaphragm.

According to a further feature of the invention, said second shaping means are constituted by a diaphragm presenting a circular opening of diameter at least substantially equal to the smallest dimension of the section of the beam leaving the source.

The first and second focussing optics are advantageously lenses having the same focal distance.

BRIEF DESCRIPTION OF THE DRAWINGS

The invention will be more readily understood on reading the following description with reference to the accompanying drawings, in which.

DETAILED DESCRIPTION OF THE PREFERRED EMBODIMENT

Figure 1:
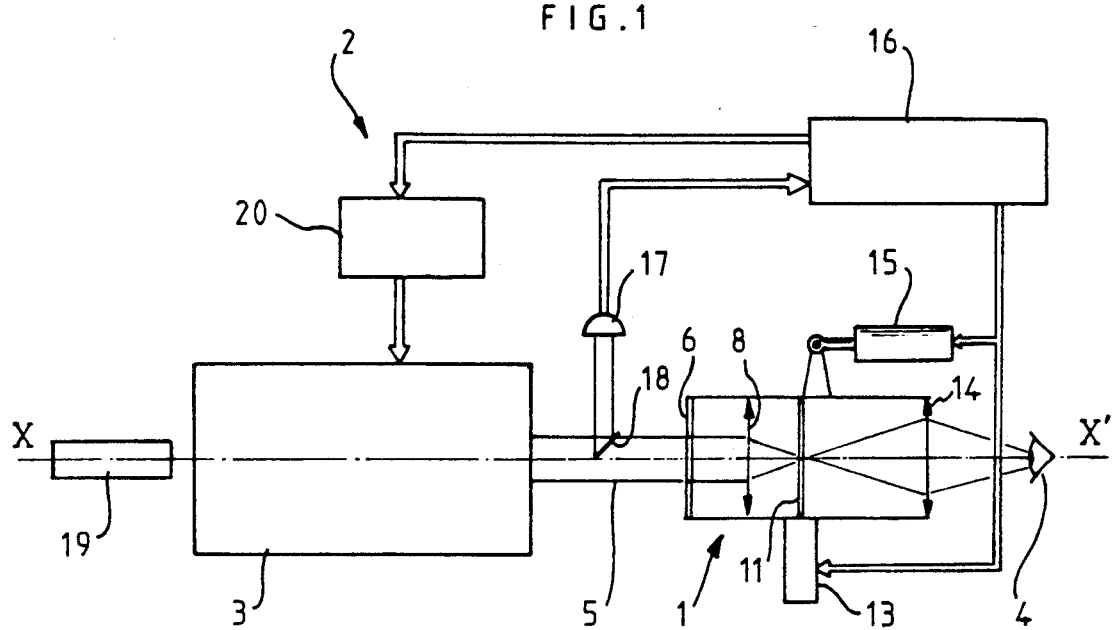
FIG. 1 is an overall block diagram of a surgical apparatus incorporating the optical system of the invention.

In these Figures, like references designate like elements.

Referring now to the drawings, in the embodiment illustrated, the optical system 1 forms part of a surgical apparatus 2 for modifying the curvature of the cornea.

The optical system 1 is adapted to be disposed between a source of ultraviolet light 3 and a target, in the present case an eye 4.

The light source 3, in this application of the invention to the surgical apparatus 2, is capable of emitting a homogeneous light beam 5 of which the wave length is close to 0.2 micrometer, for example an excimer laser generator, of the argon-fluorine mixture type.

Figure 2:
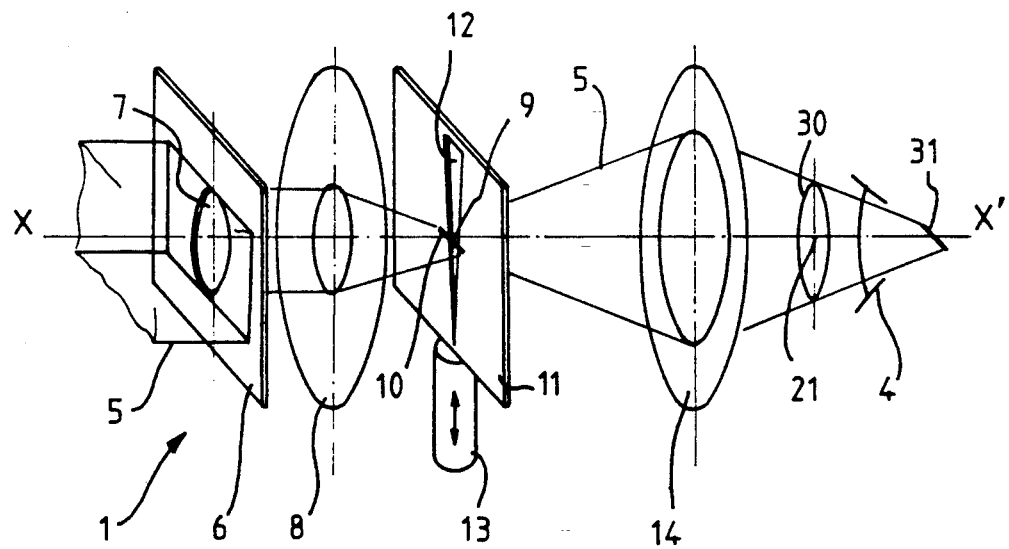
FIG. 2 is a schematic view in perspective of the optical system of the invention.

Referring more particularly to FIG. 2, the optical system 1 successively comprises, in the direction of propagation of the beam 5 (i.e. from left to right in FIG. 2):

a first diaphragm 6 presenting a circular opening 7 of diameter at least substantially equal to the smallest dimension of the section of beam 5 on leaving the source 3 (in the example illustrated, the section of the beam on leaving the source 3 being rectangular, the diameter of the opening 7 will be equal to the width of said beam 5);

a first lens 8 for focussing the light beam 5, said beam presenting, thanks to the diaphragm 6 which may for example be located at the object focus of the lens 8, a circular section and, due to characteristics inherent in the light beam, presenting at the image focus 9 of the lens 8 a section of oblong shape, which may be represented schematically by the "bar" 10 of FIG. 2;

a second diaphragm 11 whose opening 12 is in the form of a V-shaped slot disposed transversely to the direction of propagation X—X' of the beam 5 and of which the width varies between zero and the length of the bar 10, said diaphragm 11 being disposed at the image focus 9 of the lens 8 and thus being able to remove a variable part of the area of the section of beam 5 at said image focus when the diaphragm is displaced transversely to said direction X—X' with the aid of means 13; and a second lens 14 which refocusses the light beam in the direction of the target, and which may be located, with respect to the diaphragm 11, at a distance equal to twice the focal distance of the lens 14, the lenses 8 and 14 being able to have the same focal distance.

For any relative displacement, with the aid of means 15, of the eye 4 and of the optical system 1 in the image space of the system, said area removed by the diaphragm 11 is thus adjustable so as to obtain, on the eye, a section of the beam 5 which remains at least substantially circular, as will be seen in greater detail hereinafter.

The surgical apparatus 2 makes it possible to modify at least in part the curvature of the cornea of the eye 4 by ablation of a zone thereof in the form of a lenticular plate of radially variable thickness, the beam of ultraviolet light of wave length close to 0.2 micrometer allowing photodecomposition of the corneal matter, and the optical system 1 making it possible to direct said beam onto the zone of cornea to be eliminated and forming a light spot on a part of said zone, said spot being capable of scanning the whole of said cornea zone.

In addition to the light source 3 and the optical system 1, the surgical apparatus 2 comprises:

an electronic computer 16 for controlling the process of operation of said apparatus, and in particular for controlling the optical system 1, more especially the means 13 for displacement of the diaphragm 11 transversely to the direction of propagation X—X' of the beam 5 and the means 15 for displacing the system 1, or a part thereof such as the lens 14, with respect to the eye 4;

a photodetector 17, associated with a semi-transparent mirror 18, and intended to furnish the computer 16 with the data relative to the energy of the pulses of the beam 5;

an aligning laser 19, for example of the helium-neon type, allowing a correct positioning of the beam 5 on the cornea;

a device 20 for controlling the source 3, itself controlled by the computer 16; and an automatic keratometer (not shown) which measures in real time the curvature of the cornea and transmits its measurements to the computer, and a slit lamp (not shown) which allows the surgeon to observe the cornea during the operation.

The computer is programmed to control the optical system as a function of the law of variation of thickness desired for the plate to be eliminated from the cornea, and it executes the corresponding sequences of operations, taking into account the data furnished thereto by the keratometer and the photodetector.

Thanks to the optical system 1 of the invention, there is obtained in the image space of the system (i.e. the space in which the eye 4 on which the operation is to take place is physically located), a beam of which the section develops from a purely circular shape 30 at the conjugated plane 21 of the diaphragm 6 to a shape 31 corresponding to that of the oblong section of the beam 5 at the image focus 9 of the first lens 8, thus presenting a more and more accentuated ellipticity which is in fact corrected, according to the invention, thanks to diaphragm 11 with V-shaped opening, which is capable of removing a variable area of said oblong section thus maintaining the ellipticity within a predetermined limit at the level of the target 4.

Figure 3A:
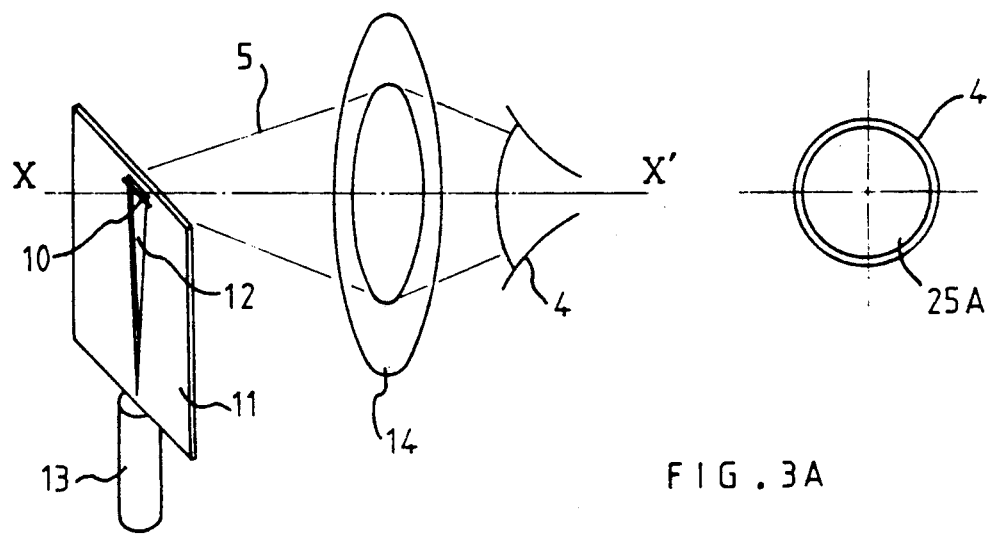
FIG. 3A illustrates the appropriate positioning of the components of the optical system when it is desirable to make a large light spot on the target eye.

In other words, if the target (eye 4) is in the conjugated plane of the diaphragm 6 through the whole of the optical system, the section of the beam 5 being at that point circular, the diaphragm 11 will be adjusted transversely to the direction of propagation X—X' of the beam so that it removes a maximum of said oblong section, the zone of maximum opening of the slot 12 then being opposite said oblong section ("bar" 10) (FIG. 3A). The light spot 25A shown on the right-hand part (front view) of FIG. 3A is then obtained on the target 4.

Figure 3B:
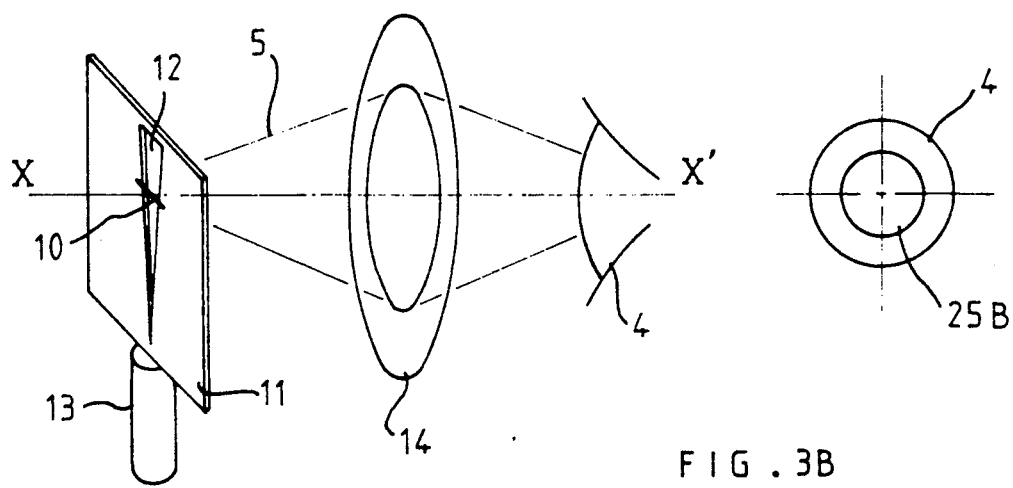
FIG. 3B illustrates the appropriate positioning of the components of the optical system when it is desirable to make a medium-sized light spot on the target eye.
Figure 3C:
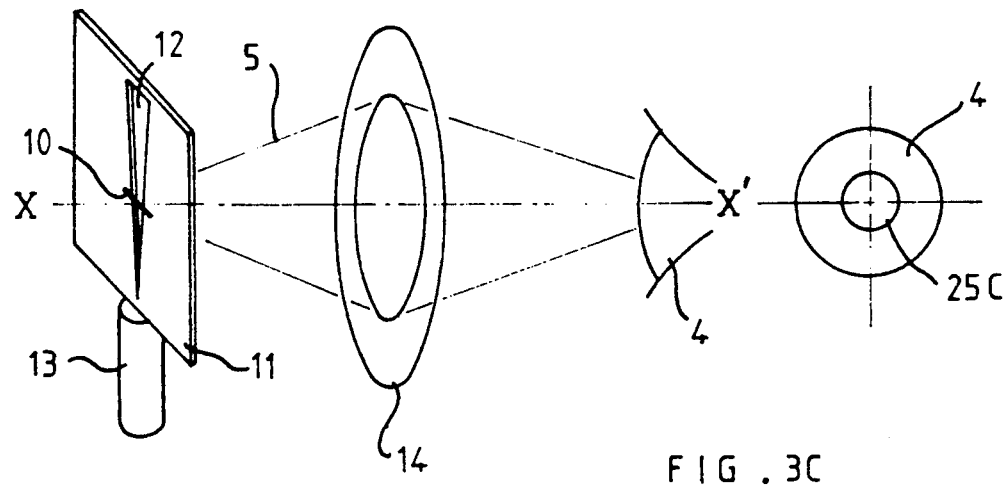
FIG. 3C illustrates the appropriate positioning of the components of the optical system when it is desirable to make a small light spot on the target eye.

When the distance between the second lens 14 and the target (eye 4) increases, the section of the beam at the level of the target would tend (without diaphragm) to become more and more elongated. In order to maintain a substantially circular section, the diaphragm 11 will be adjusted transversely to the direction of propagation X—X' of the beam so as to remove a portion of area of said oblong section which decreases when the target moves away from the conjugated plane of the diaphragm 6 through the whole of the optical system 14 (and which corresponds to light spots 25B and 25C of FIGS. 3B and 3C).

In addition, this device maintains at a substantially constant level the light energy by impulse and per surface unit received by the target, this ensuring a process of photoablation identical to itself for the whole duration of the operation.

In this way, the optical system of the invention ensures at every instant a filtering making it possible to obtain a maximum optical power taking into account the condition of maintaining the symmetry of revolution of the light spot on the target. The overall duration of the surgical operation is thus minimized, and the conditions of photodecomposition vary within a smaller interval.

What is claimed is:

1. An optical system to be disposed between a source capable of emitting a divergent beam of light and a target, said optical system including first optics for focusing said beam of light, wherein at the upstream focal point of said first optics, said beam produces an image which is at least substantially circular in section, but wherein due to the divergent nature of the beam of light, produces an image at the downstream focal point of said first focusing optics which has a section of oblong shape, wherein said optical system successively comprises, in the direction of propagation of said beam, downstream of said first optics, first shaping means disposed near the focal point of said first focusing optics, said first shaping means obscuring a variable part of said beam, and second focusing optics, with the result that, for any relative displacement of the target and said optical system wherein said target is within about one focal length of said second focusing optics, the area of said beam removed by said first shaping means is adjustable so as to obtain, at the level of the target, a section of beam which remains at least substantially circular,
wherein said first shaping means are constituted by a diaphragm disposed transversely to the direction of propagation of the beam, said diaphragm including a slot, the width of said slot uninterruptingly varying between zero and the largest dimension of the oblong section of the beam at the location of said first shaping means, and said optical system further comprises means for displacing said diaphragm relative to the rest of said system transverse to the direction of propagation of the beam.

2. The optical system of claim 1, wherein said second focussing optics are located, with respect to said first shaping means at a distance equal to at least substantially twice the focal distance of said second optics.

3. The optical system of claim 1, wherein said means for displacing said diaphragm can move said diaphragm continuously.

4. The optical system of claim 1, wherein said displacement means are associated with said diaphragm.

5. The optical system of claim 1, wherein the first and second focussing optics are lenses having the same focal length.

6. The optical system of claim 1, wherein said optical system further comprises, between said source and said first focusing optics, second means for shaping said beam, on leaving said source, along an at least substantially circular section.

7. The optical system of claim 6, wherein said second shaping means are disposed upstream from said first focusing optics a distance of about one focal length of said first focusing optics.

8. The optical system of claim 6, wherein said second shaping means are constituted by a diaphragm having a circular opening of diameter at least substantially equal to the smallest dimension of the section of the beam leaving the source.

* * * * *